United States Patent [19]

Bokerman et al.

[11] Patent Number: 4,740,607

[45] Date of Patent: Apr. 26, 1988

[54] REMOVAL OF OLEFINS FROM ORGANOHALOSILANES

[75] Inventors: Gary N. Bokerman, Madison, Ind.; Ollie W. Marko; Robert D. Steinmeyer, both of Carrollton, Ky.

[73] Assignee: Dow Corning Corporation, Midland, Mich.

[21] Appl. No.: 103,474

[22] Filed: Oct. 1, 1987

[51] Int. Cl.$^4$ .............................................. C07F 7/08
[52] U.S. Cl. .................................... 556/466; 556/479
[58] Field of Search ................................ 556/479, 466

[56] References Cited

U.S. PATENT DOCUMENTS 2,823,218  2/1958  Speier et al. .................... 556/479 X

FOREIGN PATENT DOCUMENTS 50-39649  12/1975  Japan ........................... 856/466 UX
59-137312  8/1984  Japan ........................... 556/466 UX

*Primary Examiner*—Paul F. Shaver
*Attorney, Agent, or Firm*—Carl A. Yorimoto

[57] ABSTRACT

A process for purifying alkylhalosilanes to reduce the content of olefinic impurities is described. The process comprises (A) contacting crude alkylhalosilanes, containing as a minor portion the olefinic impurities, with a hydrogen-containing halosilane and a soluble compound of a Group VIII metal; (B) facilitating reaction of the olefins with the hydrogen-containing silicon compound in contact with the Group VIII metal compound to form linear or branched silalkanes, said silalkanes having the formula, $$R^{ii}{}_m A_n SiX_p; \text{ and}$$

(C) separating the alkylhalosilanes from the silalkanes formed in the reaction in (B).

20 Claims, No Drawings

REMOVAL OF OLEFINS FROM ORGANOHALOSILANES

BACKGROUND OF THE INVENTION

This invention relates to the purification of organohalosilanes. More specifically, this invention relates to a means for chemically converting olefin impurities in organohalosilanes and isolating and recovering the purified organohalosilane.

High-purity organohalosilanes are needed for the ever-increasing quality needs of the industrial manufacture of other organosilanes and organopolysiloxanes. In the preparation of organohalosilanes via the direct reaction of an organic halide with silicon, the crude organohalosilane mixture contains minor amounts of the whole spectrum of hydrocarbon impurities. The olefinic components in many cases cause a separation problem with the commonly used practice of isolating by distillation the desired organohalosilanes contained in the crude reaction product of the direct reaction, the olefin components having boiling points very close to the various organohalosilanes. As impurities in the isolated organohalosilanes, these olefinic materials pose serious quality problems.

Olefins are known to cause color problems in the preparation of organosilane and polyorganosiloxane intermediates and products. In the processing environment to which the direct process crude is exposed, the olefinic materials are easily converted to chlorocarbons by reaction with hydrogen chloride. Chlorocarbons create a problem due to their thermal instability, potentially decomposing into an olefin and hydrogen chloride. As an example, an organohalosilane containing low levels of a chlorocarbon can be converted to a polyorganosiloxane via hydrolysis with the chlorocarbon surviving early process steps, only to dehydrohalogenate causing an acidity problem with the hydrolyzate product and also color problems due to the olefin formed.

Motomiya, Japanese Patent Publication No. 50-39649, published Dec. 18, 1975, discloses a method for purification of organohalosilanes in which a Lewis acid or a metal hydroxide is used to convert unsaturated and saturated hydrocarbon impurities to polymers, facilitating recovery of purified organohalosilanes. Motomiya demonstrates that the presence of a hydrogen-containing silane compound is not necessary for the conversion of the hydrocarbons to a polymer to proceed. No mention is made of the reaction of an olefinic material with a hydrogen-containing silicon compound in which there is at least one hydrogen atom attached to a silicon atom in the presence of a Group VIII metal catalyst to form a higher-boiling organohalosilane to facilitate isolation and separation of the desired organohalosilane with enhanced purity.

Clay et al., Japanese Patent Publication No. 59-137312, published Aug. 7, 1984, discloses a method for purification of chlorosilanes in which chlorohydrides of elements from Group III or IV of the Periodic Table are contacted with chlorine to convert these chlorohydrides to chlorides to facilitate separation of these impurities from the desired chlorosilanes via distillation. No mention is made of applying this method to the removal of olefinic materials from organohalosilanes.

SUMMARY OF THE INVENTION

It is an objective of the instant invention to provide a simpler means for isolating and removing olefinic impurities from organohalosilanes than the present use of distillation.

The reaction of olefinic material with silane materials containing at least one hydrogen atom attached to silicon to form higher molecular weight organosilanes is well-known in the art. However, the application of this chemistry to an industrial process for purification of organohalosilanes is the point of novelty of the instant invention.

DESCRIPTION OF THE INVENTION

In accordance with the instant invention there is described a process for purifying organohalosilanes by reducing the olefin content under conditions that will be delineated herein. What is described, therefore, is a process for purifying alkylhalosilanes to reduce the content of olefin impurities, wherein said alkylhalosilanes have the formula, $$R^i_a SiX_{4-a}$$

wherein each $R^i$ is independently selected from alkyl groups containing 1, 2, 3, or 4 carbon atoms; and X is a halogen atom; and a has a value of 1, 2, or 3, and wherein said olefin impurities are selected from a group consisting of linear and branched olefins containing 2 to 10 carbon atoms; said process comprising (A) contacting crude alkylhalosilanes, said crude alkylhalosilanes being a mixture comprising alkylhalosilanes as a major portion and olefin impurities as a minor portion, in a liquid phase with a hydrogen-containing silicon compound and a catalyst which promotes a hydrosilation reaction between the olefins and the hydrogen-containing silicon compound, said hydrogen containing silicon compound having the formula, $$R^{ii}_m H_n SiX_p,$$

wherein each $R^{ii}$ is independently selected from alkyl groups containing 1, 2, 3, or 4 carbon atoms; X is a halogen atom; m has a value of 0, 1, 2, or 3; n has a value of 1, 2, 3, or 4; p has a value of 0, 1, 2, or 3; and the sum of (m+n+p) must equal 4; wherein said catalyst is a soluble compound of a Group VIII metal;

(B) facilitating reaction of the olefins with the hydrogen-containing silicon compound in contact with the catalyst to form linear or branched silalkanes, said silalkanes having the formula, $$R^{ii}_m A_n SiX_p,$$

wherein each $R^{ii}$ is independently selected; $R^{ii}$, X, m, n, and p are defined above; and A is an alkyl group containing 2 to 10 carbon atoms; and Since the olefins have been converted to silalkanes, the quality problems, such as formation of chlorocarbons and the thermal instability of the chlorocarbons and the related acidity problems, will have been significantly reduced. The silalkanes may be in low enough quantities in the organohalosilane to be carried along without subsequent quality problems. Thus, separation of the silalkanes is not necessary in all cases.

However, where quality requirements dictate that the silalkane be isolated and separated from the alkylhalosilane, the process of the instant invention will further comprise separating the alkylhalosilanes from the silakanes formed.

The alkylhalosilane can be, for example, trimethylchlorosilane, dimethyldichlorosilane, methyltrichlorosilane, dimethyldibromosilane, triethylchlorosilane, diethyldichlorosilane, methylethyldichlorosilane, or tert-butyldimethylchlorosilane. The preferred alkylhalosilanes are ethyl and methyl-containing chlorosilanes.

The hydrogen-containing silicon compound can be, for example, silane, chlorosilane, dichlorosilane, trichlorosilane, methylsilane, dimethylsilane, trimethylsilane, methyldichlorosilane, dimethylchlorosilane, methylbromosilane, ethyldichlorosilane, or triethylsilane.

The olefin can be, for example, ethylene, propylene, 2-methylpropene-1, butene-1, pentene 1,2 methylbutene-1,2-methylbutene-2,4-methylpentene-1, hexene-1, or octene-1. Th be in a terminal or an internal position, Hydrosilation reactions favor the reaction of the terminal bond. However, under the conditions of reaction of the instant invention, it is believed that the internal double bond will migrate to a terminal position and undergo subsequent hydrosilation.

The catalyst, a soluble compound of a Group VIII metal, is selected from a group consisting of compounds of platinum, palladium, rhodium, and ruthenium. The catalyst can be, for example, chloroplatinic acid, hydrated palladium chloride, hydrated rhodium chloride, hydrated ruthenium chloride, palladium nitrate, rhodium carbonyl chloride, tris(triphenylphosphine)rhodium chloride, or a platinum-organosiloxane complex. The preferred catalyst is a platinum compound. For the purposes of the instant invention the term "soluble compound of a Group VIII metal" means a compound of the metal which is soluble in the mixture of crude alkylhalosilanes and the hydrogen-containing silicon compound at the conditions of contact and reaction so that a homogeneous, liquid reaction system is present.

The use of Group VIII metals supported on a solid substrate was evaluated as a catalyst for the conversion of olefins to silakanes. As shown in the examples, infra, this was not successful. The primary products formed from the olefins were chlorocarbons.

The silakanes can be, for example, tetraethylsilane, methylpropyldichlorosilane, butyltribromosilane, ethyl(2-methylpropyl)dichlorosilane, or methyl(2-methylbutyl)dichlorosilane.

The crude alkylhalosilane is a mixture containing as a major portion as much as 75 to greater than 99 weight percent of the desired alkylhalosilanes. As one minor portion of the crude mixture, the olefins could typically be present at concentrations of 10 parts per million on a weight basis up to 1 to 2 weight percent of the crude mixture. A second minor portion of the crude alkylhalosilanes can be the hydrogen-containing silicon compound which can comprise greater than 1 weight percent of the mixture. The present invention is believed to be effective at removing olefins down to levels of about 10 parts per million (ppm) of the total crude content on a weight basis.

The hydrogen-containing silicon compound is normally a minor portion of the crude alkylhalosilanes. However, in order to assure the presence of a sufficient amount of the hydrogen-containing silicon compound to maximize the conversion of olefins to silakanes, a hydrogen-containing silicon compound may be added to the crude alkylhalosilanes. For the purposes of the instant invention the hydrogen-containing silicon compound should be present in the reaction mixture at a concentration at which the molar concentration of hydrogen atoms attached to silicon is in a stoichiometric excess relative to the olefin impurities. Stoichiometric excesses of hydrogen atoms attached to silicon relative to the olefin impurities of greater than 1000 to 2000 percent may be necessary to maximize the conversion of olefins to silakanes. It is understood that greater stoichiometric excesses may be utilized; however, no additional benefit is expected. Conversely, quantities less than the stoichiometric amount of the hydrogen-containing silicon compound may be used with the expected lower conversion of olefins to silakanes.

The catalyst, as a platinum-siloxane complex, has been demonstrated (in the examples, infra) to be effective at essentially quantitatively converting all olefins to silakanes in a crude alkylhalosilane mixture containing a hydrogen-containing silicon compound at platinum levels of approximately 100 ppm on a weight basis relative to the crude mixture. Based upon known art on hydrosilation reactions, it is projected that concentrations of the Group VIII metal of 10 ppm or less are effective at facilitating similar conversion of olefins to silakanes. Catalyst concentrations lower than 10 ppm of the Group VIII metal are believed to be effective; however, such low concentrations of catalyst could be easily rendered ineffective by small concentrations of impurities or other conditions that would inhibit the action of or poison the catalyst. Concentrations of greater than 100 ppm of the Group VIII metal will be effective, but no advantage is seen and an economic disadvantage would lead one away from these higher concentrations. Therefore a preferred catalyst concentration is in the range of about 10 to 100 ppm of the Group VIII metal based upon the weight of the crude alkylhalosilane mixture.

The hydrosilation reaction of hydrogen-containing silicon compounds and olefins is know to occur at temperatures above ambient. Therefore, contacting of the crude alkylhalosilanes, the hydrogen-containing silicon compound, and the catalyst should occur at a temperature of greater than about 25° C. To facilitate adequate reaction rates, temperatures in the range of about 30° to 80° C., should be utilized.

The hydrosilation reaction of hydrogen-containing silicon compounds and olefins is known to be quite rapid, the reaction being completed in a matter of minutes. However, to assure maximum conversion of the olefins to silakanes, a contact time of greater than about 10 minutes is preferred. Contact times in the range of 10 to 60 minutes are more preferred. It is understood that shorter contact times may be utilized; however, the results will be a lesser conversion of the olefins to silakanes.

Many of the alkylhalosilanes and olefins have low-boiling points relative to ambient temperature. To assure that the mixture of crude alkylhalosilanes and hydrogen-containing silicon compounds remain liquid during the course of reaction, pressures greater than atmospheric pressure should be maintained in the contact/reaction facilities. Pressure in the range of from about 40 to 80 psig should be utilized. Pressure can be maintained by the vapor pressure of the liquid mixture or by addition of an inert gas such as nitrogen to the system.

Contacting the crude alkylhalosilanes with the catalyst can be effected by known techniques for carrying out liquid phase chemical reactions. Contact can be made in a batch or continuous mode. A batch mode can be a conventional stirred tank reactor. A continuous mode can be a stirred tank reactor with continuous feed and product overflow or a column type reactor.

"Facilitating the reaction of the olefins with the hydrogen-containing silicon compound" for the purposes of the instant invention means providing such facilities as adequate agitation to assure sufficient contact among the crude alkylhalosilanes, the hydrogen-containing silicon compound, and the catalyst. Facilities for heat transfer to add or remove heat from the reaction mixture may also be provided.

Separating the alkylhalosilanes with reduced olefin content from silalkanes can be facilitated by such known separation means as distillation. The conversion of olefins in crude alkylhalosilanes to silalkanes and the subsequent recovery by distillation yields a alkylhalosilane mixture in which the olefin content can be reduced by greater than about 95 percent.

So that those skilled in the art can better understand the instant invention, the following examples are present. These examples are presented to be illustrative and are not to be construed as limiting the instant invention as delineated in the claims.

EXAMPLE 1 (Not within the scope of the instant invention)

A liquid mixture which consisted of:
96.8 weight percent dimethyldichlorosilane
3.1 weight percent methyldichlorosilane
0.1 weight percent 2-methylbutene-2
was prepared. The liquid mixture was place in a standard batch reactor with agitation. No catalyst was used. The reaction mixture was held at a temperature of approximately 25° C. for a period of approximately 15 minutes. The mixture in the reactor was sampled, and the sample was analyzed by gas chromatography. From the results of this analysis, the concentration of methyldichlorosilane, olefins, chlorocarbons, and silalkanes is reported in Table 1. The results are reported in area percent (%) and parts per million (ppm).

TABLE 1

| Methyldichlorosilane | 2.2% |
| --- | --- |
| 2-Methylbutene-2 | 0 ppm |
| Pentanes | 25 |
| Heptanes | 183 |
| 2-Chloro-2-methylbutane | 1608 |
| Silalkanes | 0 |

The above results demonstrate that without a catalyst silalkanes are not formed when olefins in a alkylhalosilane mixture are contacted with a hydrogen-containing silicon compound. The olefins appear to react with the hydrogen chloride found in the alkylhalosilanes to form chlorocarbons. The chlorocarbons are an undesirable impurity in alkylhalosilanes.

EXAMPLE 2

A portion of the mixture of dimethyldichlorosilane, methyldichlorosilane, and olefin utilized in Example 1 was added to the batch reactor. To this mixture was added a platinum/siloxane complex as a hydrosilation catalyst. The platinum/siloxane complex was the reaction product of chloroplatinic acid and divinyltetramethyldisiloxane. The platinum content of the complex was 4.2 weight percent. An amount of the catalyst was added to the chlorosilane/olefin mixture to yield a platinum concentration in the mixture of 100 ppm on a weight basis relative to the total mixture. The reaction was allowed to proceed at a temperature of about 25° C. for a period of about 15 minutes. The mixture in the reactor was sampled and analyzed as in Example 1. Table 2 is a summary of this analysis, using the notation of Example 1.

TABLE 2

| Methyldichlorosilane | 0.8% |
| --- | --- |
| 2-Methylbutene-2 | 0 ppm |
| Pentanes | 310 |
| Heptanes | 181 |
| 2-Chloro-2-methylbutane | 40 |
| Silalkanes | 1735 |

The above results demonstrate that olefins in an alkylhalosilane mixture are converted to silalkanes via the hydrosilation reaction with hydrogen-containing silicon compounds with little formation of objectionable chlorocarbons.

EXAMPLE 3

The liquid mixture of dimethyldichlorosilane, methyldichlorosilane, olefin, and platinum catalyst similar to that used in Example 2 was passed through a stainless steel column that was heated to 80° C. The liquid mixture was fed at a rate such that the liquid residence time in the column was about 15 minutes. The effluent from column was sampled and analyzed as in Example 1. Table 3 is a summary of this analysis, using the notation of Example 1.

TABLE 3

| Methyldichlorosilane | 1.4% |
| --- | --- |
| 2-Methylbutene-2 | 0 ppm |
| Pentanes | 94 |
| Heptanes | 167 |
| 2-Chloro-2-methylbutane | 34 |
| Silalkanes | 2491 |

The above results further demonstrate that olefins in an alkylhalosilane mixture are converted to silalkanes via the hydrosilation reaction with hydrogen-containing silicon compounds with little formation of objectionable chlorocarbons. The results of Examples 2 and 3 demonstrate that the reaction to convert olefins in crude alkylhalosilanes to silalkanes can be effected in either of batch or a continuous mode.

EXAMPLE 4 (Not within the scope of the instant invention)

Two liquid mixtures of dimethyldichlorosilane containing methyldichlorosilane, olefinic material, and tetramethylsilane were prepared. These samples, designated as Samples A and B, respectively, are characterized by the content of these above additives in weight percent or ppm as follows:

| Sample | A | B |
| --- | --- | --- |
| Methyldichlorosilane | 3.6% | 3.4% |
| 2-Chloro-2-Methylbutene | 2483 ppm | — |
| 2-Methyl-2-Butene | — | 2750 ppm |
| Tetramethylsilane | 5253 ppm | 4517 ppm |

These two samples were individually passed through a heated column of 5 weight percent platinum on coconut shell granules at 100° C. and 60 minutes residence time. The coconut shell granules had a particle size of −4 to +8 mesh and a surface area of 1000 m²/g. In both cases, very little conversion of olefins to silalkanes was effected. Additionally, of the olefins converted, the product was mainly other olefins and undesirable chlorocarbons.

The above results demonstrate that supported platinum on carbon is not an effective catalyst for the reaction of olefins in crude organohalosilanes with a hydrogen-containing silane for forming silalkanes.

What is claimed is:

1. A process for purifying alkylhalosilanes to reduce the content of olefin impurities, wherein said alkylhalosilanes have the formula, $$R^i_a SiX_{4-a}$$

wherein each $R^i$ is independently selected from alkyl groups containing 1, 2, 3, or 4 carbon atoms; and X is a halogen atom; and a has a value of 1, 2, or 3, and wherein said olefin impurities are selected from a group consisting of linear and branched olefins containing 2 to 10 carbon atoms; said process comprising
   (A) contacting crude alkylhalosilanes, said crude alkylhalosilanes being a mixture comprising alkylhalosilanes as a major portion and olefin impurities as a minor portion, in a liquid phase with a hydrogen-containing halosilane and a catalyst which promotes a hydrosilation reaction between the olefins and the hydrogen-containing silicon compound, said hydrogen containing silicon compound having the formula, $$R^{ii}_m H_n SiX_p,$$

wherein each $R^{ii}$ is independently selected from alkyl groups containing 1, 2, 3, or 4 carbon atoms; X is a halogen atom; m has a value of 0, 1, 2, or 3; n has a value of 1, 2, 3, or 4; p has a value of 0, 1, 2, or 3; and the sum of (m+n+p) must equal 4;
   wherein said catalyst is a soluble compound of a Group VIII metal; and
   (B) facilitating reaction of the olefins with the hydrogen-containing silicon compound in contact with the catalyst to form linear or branched silalkanes, said silalkanes having the formula, $$R^{ii}_m A_n SiX_p,$$

wherein each $R^{ii}$ is independently selected; $R^{ii}$, X, m, n, and p are defined above; and A is an alkyl group containing 2 to 10 carbon atoms.

2. A process according to claim 1, further comprising (C) separating the alkylhalosilanes from the silalkanes formed in the reaction in (B).

3. A process according to claim 1, wherein the hydrogen-containing silicon compound is a minor portion of the crude alkylhalosilanes.

4. A process according to claim 1, wherein the hydrogen-containing silicon compound is added to the crude alkylhalosilanes.

5. A process according to claim 3, wherein additional hydrogen-containing silicon compound is added to the crude alkylhalosilanes.

6. A process according to claim 1, wherein the catalyst is selected from a group consisting of compounds of platinum, palladium, rhodium, and ruthenium.

7. A process according to claim 6, wherein the the catalyst is a platinum compound.

8. A process according to claim 3, wherein the hydrogen-containing silicon compound is present in the crude alkylhalosilanes at a concentration at which the molar concentration of hydrogen atoms attached to silicon is in a stoichiometric excess relative to the olefin impurities.

9. A process according to claim 4, wherein the hydrogen-containing silicon compound is added to the crude alkylhalosilane to a concentration at which the molar concentration of hydrogen atoms attached to silicon is in a stoichiometric excess relative to the olefin impurities.

10. A process according to claim 5, wherein the hydrogen-containing silicon compound is present in the crude alkylhalosilanes at a concentration at which the molar concentration of hydrogen atoms attached to silicon is in a stoichiometric excess relative to the olefin impurities.

11. A process according to claim 1, wherein the olefin is present in the crude alkylhalosilanes at a concentration of greater than about 10 parts per million (ppm) on a weight basis.

12. A process according to claim 1, wherein the catalyst is present at a Group VIII metal concentration greater than about 10 parts per million (ppm) on a weight basis relative to the crude alkylhalosilanes.

13. A process according to claim 1, wherein the crude alkylhalosilanes and the hydrogen-containing silicon compound are contacted with the catalyst at a temperature of greater than about 25° C.

14. A process according to claim 1, wherein the crude alkylhalosilanes, the hydrogen-containing silicon compound, and the catalyst are in contact for greater than about 10 minutes.

15. A process according to claim 1, wherein contacting said crude alkylhalosilanes with said catalyst is effected at a pressure of atmospheric pressure or greater.

16. A process according to claim 2, wherein separating the alkylhalosilanes from the silalkanes is facilitated by distillation.

17. A process according to claim 1, wherein the crude alkylhalosilane, the hydrogen-containing silicon compound and the catalyst are in contact for greater than about 1 minute at a temperature of greater than about 25° C. at a pressure of greater than atmospheric pressure; wherein the hydrogen-containing silicon compound is present in the crude alkylhalosilanes at a concentration at which the molar concentration of hydrogen atoms attached to silicon is in a stoichiometric excess relative to the olefin impurities; wherein the catalyst is present at a Group VIII metal concentration of greater than about 10 parts per million on a weight basis relative to the crude alkylhalosilanes; and wherein the alkylhalosilanes are separated and recovered by distillation.

18. A process according to claim 17, wherein the crude alkylhalosilanes and the catalyst are in contact for a time in a range from about 10 to 60 minutes at a temperature in a range from about 30° to 100° C.; wherein the hydrogen-containing silicon compound is present at a concentration at which the molar concentration of hydrogen atoms attached to silicon is in a stoichiometric excess of greater than about 1000 percent relative to the olefin impurities; wherein the catalyst is present at a Group VIII metal concentration in a range from about 10 to 100 parts per million on a weight basis relative to the crude alkylhalosilanes; and wherein the level of olefin impurities in the recovered alkylhalosilane is reduced by greater than 95 percent.

19. A process according to claim 18, wherein the crude alkylhalosilanes are methylchlorosilanes, the hydrogen-containing silicon compound is methyldichlorosilane, and the catalyst is a compound of platinum.

20. A process according to claim 19, wherein the olefin impurity is 2-methylbutene-2.

* * * * *

UNITED STATES PATENT AND TRADEMARK OFFICE
CERTIFICATE OF CORRECTION

PATENT NO. : 4,740,607

DATED : April 26, 1988

INVENTOR(S) : Gary N. Bokerman, Ollie W. Marko, and Robert D. Steinmeyer

It is certified that error appears in the above-identified patent and that said Letters Patent is hereby corrected as shown below:

In the specification, Column 2, lines 47-48, "wherein said catalyst is a soluble compound of a Group VIII metal;" should not be in boldface type.

Column 3, lines 17-18, delete "pentene 1,2 methylbutene-1,2-methylbutene-2, 4-methylpentene-1" and insert therefor -- pentene-1, 2-methylbutene-1, 2--methylbutene-2, 4-methylpentene-1 --.

Column 3, line 19, delete "Th be in a terminal or internal position," and insert therefor -- "The olefinic bond may be in a terminal or an internal position. --

Signed and Sealed this

Seventh Day of March, 1989

Attest:

DONALD J. QUIGG

*Attesting Officer*  *Commissioner of Patents and Trademarks*